(12) United States Patent
Vadakke Matham et al.

(10) Patent No.: US 10,799,113 B2
(45) Date of Patent: Oct. 13, 2020

(54) PROBE FOR IRIDOCORNEAL ANGLE IMAGING

(71) Applicants: NANYANG TECHNOLOGICAL UNIVERSITY, Singapore (SG); SINGAPORE HEALTH SERVICES PTE LTD, Singapore (SG)

(72) Inventors: Murukeshan Vadakke Matham, Singapore (SG); Shinoj Vengalathunadakal Kuttinarayanan, Singapore (SG); Tin Aung, Singapore (SG); Baskaran Mani, Singapore (SG)

(73) Assignees: NANYANG TECHNOLOGICAL UNIVERSITY, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 0 days.

(21) Appl. No.: 15/514,422

(22) PCT Filed: Sep. 25, 2015

(86) PCT No.: PCT/SG2015/050341
§ 371 (c)(1),
(2) Date: Mar. 24, 2017

(87) PCT Pub. No.: WO2016/048245
PCT Pub. Date: Mar. 31, 2016

(65) Prior Publication Data
US 2017/0290508 A1 Oct. 12, 2017

(30) Foreign Application Priority Data
Sep. 25, 2014 (SG) .......................... 10201406064V (51) Int. Cl.
*A61B 3/14* (2006.01)
*A61B 3/117* (2006.01)
*G02B 23/24* (2006.01)

(52) U.S. Cl.
CPC ................ *A61B 3/117* (2013.01); *A61B 3/14* (2013.01); *A61B 3/145* (2013.01); *G02B 23/2461* (2013.01)

(58) Field of Classification Search
CPC ... A61B 3/1015; A61B 1/0638; A61B 3/1208; A61B 1/00193; A61B 1/0623;
(Continued)

(56) References Cited

U.S. PATENT DOCUMENTS 4,398,812 A    8/1983   Kelman
4,429,956 A *  2/1984   Herbert .................... A61B 1/12
                                             351/159.33

(Continued)

FOREIGN PATENT DOCUMENTS

DE    102008010577 A1   9/2009
JP      0345235 A   2/1991
(Continued)

OTHER PUBLICATIONS

Foreign Communication From a Related Counterpart Application, International Search Report and Written Opinion dated Jun. 11, 2015, International Application No. PCT/SG2015/050341 filed on Sep. 25, 2015.
(Continued)

*Primary Examiner* — Brandi N Thomas (57) ABSTRACT

A probe for iridocorneal angle imaging of an eye, the probe comprising: a distal end having a corneal contact surface; a camera having an imaging lens at the distal end and an imaging axis orthogonal to the corneal contact surface; and at least two illumination sources, each illumination source
(Continued)

having an illumination axis at an angle to the corneal contact surface such that the imaging axis and the illumination axes converge in the eye.

18 Claims, 6 Drawing Sheets

(58) Field of Classification Search
CPC ....... A61B 3/103; A61B 3/107; A61B 3/0075; A61B 3/145; A61B 1/00096; A61B 3/14; A61B 5/0084; A61B 5/0275; A61B 6/481; A61B 6/504; A61B 3/113; A61B 3/152; A61B 3/165
USPC ........ 351/200, 205, 206, 209–211, 221, 222, 351/243–246
See application file for complete search history.

(56) References Cited

U.S. PATENT DOCUMENTS

| | | | |
|---|---|---|---|
| 5,793,468 A | 8/1998 | Shalon et al. | |
| 2010/0201944 A1* | 8/2010 | Lewis | A61B 3/103 351/206 |
| 2013/0114850 A1* | 5/2013 | Publicover | G06K 9/00604 382/103 |
| 2013/0135513 A1 | 5/2013 | Choi et al. | |
| 2013/0271729 A1* | 10/2013 | Ranchod | A61B 3/125 351/206 |
| 2017/0020909 A1* | 1/2017 | Rhee | A61K 31/7056 |

FOREIGN PATENT DOCUMENTS

| | | |
|---|---|---|
| JP | 03045235 A | 2/1991 |
| WO | WO2016048245 A1 | 3/2016 |

OTHER PUBLICATIONS

Shinoj, V. K. et al., Note: A gel based imaging technique of the iridocorneal angle for evaluation of angle-closure glaucoma. Review of Scientific Instruments, Jun. 10, 2014, vol. 85, pp. 066105-1 to 066105-3 [Retrieved on Oct. 14, 2015] (001:1 0.1 063/1.4882335) (Last Accessed Mar. 21, 2017) whole document.
Shinoj, V. K. et al., Integrated flexible handheld probe for imaging and evaluation of iridocorneal angle. Journal of Biomedical Optics, Jan. 16, 2015, vol. 20, No. 1, pp. 016014-1 to 016014-5 [Retrieved on Oct. 14, 2015] (001:1 11117/11130.20.1.016014) (Last Accessed Mar. 21, 2017) whole document.
Foreign Communication From a Related Counterpart Application—European Search Report dated May 29, 2018, European Application No. 15843466.2 filed on Sep. 25, 2015.
Foreign Communication from a Related Counterpart Application, Japanese Notice of Reasons for Refusal dated May 22, 2019, Japanese Application No. 2017-516287 filed on Sep. 25, 2015.
I. Agis, "The Advanced Glaucoma Intervention Study (Alis): 7. The relationship between control of intraocular pressure and visual field deterioration," American Journal of Ophthalmology 130, 429-440 (2000).
E. M. Stone, J. H. Fingert, W. L. Alward, T. D. Nguyen, J. R. Polansky, S. L. Sunden, D. Nishimura, A. F. Clark, A. Nystuen, and B. E. Nichols, "Identification of a gene that causes primary open angle glaucoma," Science 275, 668-670 (1997).
W. P. Nolan, J. L. See, P. T. Chew, D. S. Friedman, S. D. Smith, S. Radhakrishnan, C. Zheng, P. J. Foster, and T. Aung, "Detection of primary angle closure using anterior segment optical coherence tomography in Asian eyes," Ophthalmology 114, 33-39 (2007).
T. Aung, W. P. Nolan, D. Machin, S. K. Seah, J. Baasanhu, P. T. Khaw, G. J. Johnson, and P. J. Foster, "Anterior chamber depth and the risk of primary angle closure in 2 East Asian populations," Archives of ophthalmology 123, 527-532 (2005).
V. M. Murukeshan, V. K. Shinoj, S. P, and P. Padmanabhan, "Diagnostic Sensing of Specific Proteins in Breast Cancer Cells Using Hollow-Core Photonic Crystal Fiber," in Multimodality Breast Imaging: Diagnosis and Treatment, (SPIE Press), p. 572 (2013).
V. K. Shinoj, and V. M. Murukeshan, "Hollow-core photonic crystal fiber based multifunctional optical system for trapping, position sensing, and detection of fluorescent particles," Opt. Lett. 37, 1607-1609 (2012).
J. James, V. M. Murukeshan, and L. S. Woh, "Integrated photoacoustic, ultrasound and fluorescence platform for diagnostic medical imaging-proof of concept study with a tissue mimicking phantom," Biomedical Optics Express 5, 2135-2144 (2014), http://www.opticsinfobase.org/boe/abstract.cfm?URI=boe-5-7-2135.
J. G. Fujimoto, "Optical coherence tomography for ultrahigh resolution in vivo imaging," Nature biotechnology 21, 1361-1367 (2003).
T. Scheimpflug, "Improved method and apparatus for the systematic alteration or distortion of plane pictures and mages by means of lenses and mirrors for photography and for other purposes," GB patent 1196, (1904).
R. Jain, and S. Grewal, "Pentacam: Principle and Clinical Applications," Journal of Current Glaucoma Practice 3, 20-32 (2009).
L. M. Sakata, R. Lavanya, D. S. Friedman, H. T. Aung, H. Gao, R. S. Kumar, P. J. Foster, and T. Aung, "Comparison of gonioscopy and anterior segment ocular coherence tomography in detecting angle closure in different quadrants of the anterior chamber angle," Ophthalmology 115, 769-774 (2008).
A. L. Coleman, F. Yu, and S. J. Evans, "Use of gonioscopy in medicare beneficiaries before glaucoma surgery," Journal of glaucoma 15, 486-493 (2006).
R. Azad, T. Arora, R. Sihota, P. Chandra, D. Mahajan, S. Sain, and Y. Sharma, "Retcam fluorescein gonioangiography: a new modality for early detection of angle neovascularization in diabetic retinopathy," Retina 33, 1902-1907 (2013).
S. A. Perera, M. Baskaran, D. S. Friedman, T. A. Tun, H. M. Htoon, R. S. Kumar, and T. Aung, "Use of EyeCam for imaging the anterior chamber angle," Investigative ophthalmology & visual science 51, 2993-2997 (2010).
M. Baskaran, S. A. Perera, M. E. Nongpiur, T. A. Tun, J. Park, R. S. Kumar, D. S. Friedman, and T. Aung, "Angle assessment by EyeCam, goniophotography, and gonioscopy," Journal of glaucoma 21, 493-497 (2012).
V. K. Shinoj, V. M. Murukeshan, M. Baskaran, and T. Aung, "Note: A gel based imaging technique of the iridocorneal angle for evaluation of angle-closure glaucoma," Review of scientific instruments 85, 066105 (2014).

\* cited by examiner

PROBE FOR IRIDOCORNEAL ANGLE IMAGING

CROSS-REFERENCE TO RELATED APPLICATIONS

The present application is a filing under 35 U.S.C. 371 as the National Stage of International Application No. PCT/SG2015/050341, filed Sep. 25, 2015, entitled "PROBE FOR IRIDOCORNEAL ANGLE IMAGING," which claims the benefit of and priority to Singapore Application No. 0201406064V, filed with the Intellectual Property Office of Singapore on Sep. 25, 2014, both of which are incorporated herein by reference in their entirety for all purposes.

FIELD OF THE INVENTION

This invention relates to a probe for iridocorneal angle imaging.

BACKGROUND OF THE INVENTION

The irreversible and progressive nature of glaucoma makes it one of the most serious ophthalmic diseases[1, 2]. Primary angle closure glaucoma (PACG) or acute glaucoma is one form of glaucoma where the eye's drainage canals become blocked so that intraocular pressure rises over time [3, 4]. PACG is a major form of glaucoma in Asia in contrast to western countries, it being responsible for the majority of bilateral blindness in Singapore, China and India [5, 6].

Optical imaging methods have been vital in the area of biomedical imaging for diagnosing various diseases [7-10] including diagnosis of PACG. The Pentacam® based on Scheimpflug's photography principle can be used to image anterior chamber where the imaging of an obliquely tilted object can be accomplished with maximum depth of focus and least image distortion under given conditions [11, 12]. However, assessment of iridocorneal angle cannot be done in detail using this method since direct visualization of angle recess is not available due to limitations of visible light in penetrating the depth needed.

The main pathology in PACG is a closed anterior chamber angle which is diagnosed clinically using gonioscopy, an instrument that uses a mirror system[13, 14]. Gonioscopy is a subjective procedure and the documentation is mainly through various grading procedures [13-15]. The main drawback with this method is patient discomfort and physician compliance[16]. It is noted earlier that 50% physicians do not perform gonioscopy in clinical examination[17]. Interpretation of findings requires expertise and is subject to substantial disagreement between physicians. Hence, gonioscopy is subjective and has poor to moderate agreement between clinicians, in spite of being low cost and simple to use. Multiple reflections from the lens or mirrors used along with a coupling gel cause the quality of image to be poor. In spite of this, gonioscopy remains the clinical reference standard as it allows the clinician to observe the angle structures through a cheaper instrument in the clinic and to make note of pathological findings of clinical importance.

Photographic-based documentation is the primary benefit of this technique since it allows eye care clinician to refer to the previous recordings of superficial corneal lesions or abnormalities embedded in the cornea[18]. The EyeCam™ (Clarity Medical Systems, Pleasanton, Calif., USA) technology designed for capturing wide-field photographs of the anterior and posterior segment of the eye for the disease diagnosis can also be used to image structures of anterior chamber including iridocorneal angle with proper modification[19, 20]. However, imaging of the anterior chamber angle using EyeCam™ takes longer time than gonioscopy (about 5-10 min per eye) and the device is more expensive compared to gonioscopy. A recently demonstrated gel-assisted imaging technology for angle imaging has limited flexibility and translating it into a commercial ophthalmic imaging instrument[21] is tricky. In this perspective, it is evident that it is still a challenge to develop a simple cost effective probe-based imaging scheme or instrument with which the angle of the eye can be imaged with achievable good resolution.

SUMMARY OF INVENTION

Disclosed is an eye imaging device for viewing and imaging anterior chamber of the eye through the eye cornea. The imaging device comprises an eye imaging probe with a charge-coupled device (CCD) camera having an imaging axis and a corneal contact surface. The probe is specifically designed and fabricated to image the iridocorneal angle region 100 inside the eye. This angle region is normally obstructed from direct view since it is behind the sclera and cannot be observed obliquely as the input beam from this region undergoes total internal reflection. The probe enables imaging of the anterior chamber angle region with wide-field coverage as well as in dual mode (in dark and light conditions).

The camera has variable resolution at different depths which is configured for capturing angle region of the anterior chamber of the eye when the corneal contact surface of the probe is placed on the cornea with an interfacing coupling gel. The probe and camera are connected via a flexible connection such as flexible wires to a processor which processes captured images for display through a display panel or for storage in a media storage device.

An array of illumination sources is arranged radially about the imaging axis and comprises at least one white light source and/or one Near Infra-Red (NIR) light source. The white light and NIR light sources can be switched on alternately for illuminating the interior of the eye. Preferably, the illumination axis of the light source is offset at an angle from the imaging axis such that the imaging and illumination axes converge proximately at the interior chamber of the eye when the probe is used.

According to an aspect of the invention, there is provided a probe for iridocorneal angle imaging of an eye, the probe comprising: a distal end having a corneal contact surface; a camera having an imaging lens at the distal end and an imaging axis orthogonal to the corneal contact surface; and at least two illumination sources, each illumination source having an illumination axis at an angle to the corneal contact surface such that the imaging axis and the illumination axes converge in the eye.

The angle may range from 70° to 78°.

The at least two illumination sources may be configured to emit light with a uniform distribution such that luminescence is the same when viewed from any angle.

The at least two illumination sources may comprise four light sources provided radially about the imaging axis.

The four light sources may comprise four LED.

Alternatively, the four light sources may comprise at least one white light source and at least one NIR light source. The at least one white light source and the at least one NIR light source may be configured to allow the iridocorneal angle region of the eye to be illuminated by only one of the at least one white light source and the at least one NIR light source at any time.

The at least one NIR light source may comprise at least one of: an NIR LED and a fibre-optic NIR laser source.

The camera may be connected via a flexible connection to a processor configured to process captured images for at least one of: display on a display panel and storage in a media storage device.

The imaging axis and the illumination axes may converge in the iridocorneal region of the eye.

The at least two illumination sources may be configured to have controllable intensity.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

FIGS. 4(a) to (c) are orthographic views of a second embodiment of a distal end of the probe.

DETAILED DESCRIPTION

Exemplary embodiments of the probe 10 for iridocorneal angle 100 imaging will be described below with reference to FIGS. 1 to 10(b), in which the same reference numerals are used to denote the same or similar parts.

Figure 1:
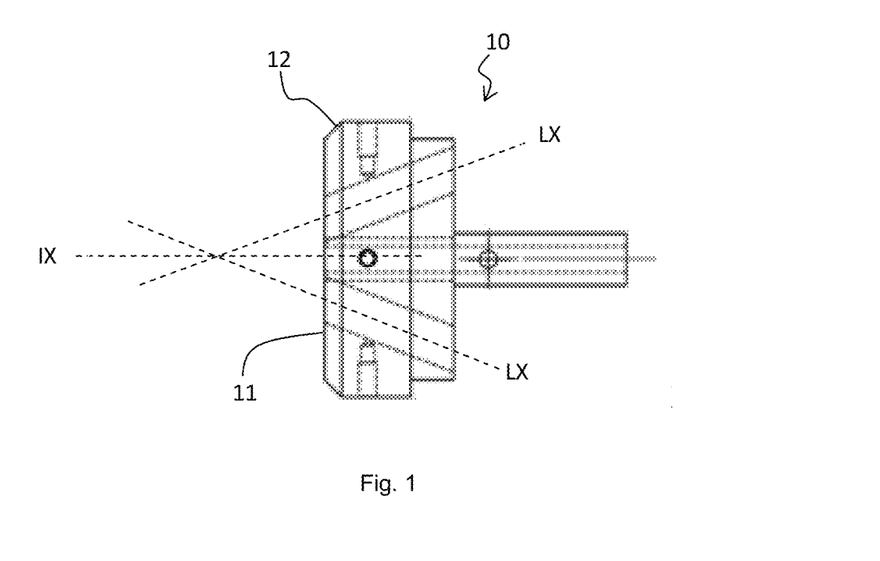
FIG. 1 is a longitudinal cross-sectional view of an exemplary embodiment of the probe of the present invention.
Figure 2:
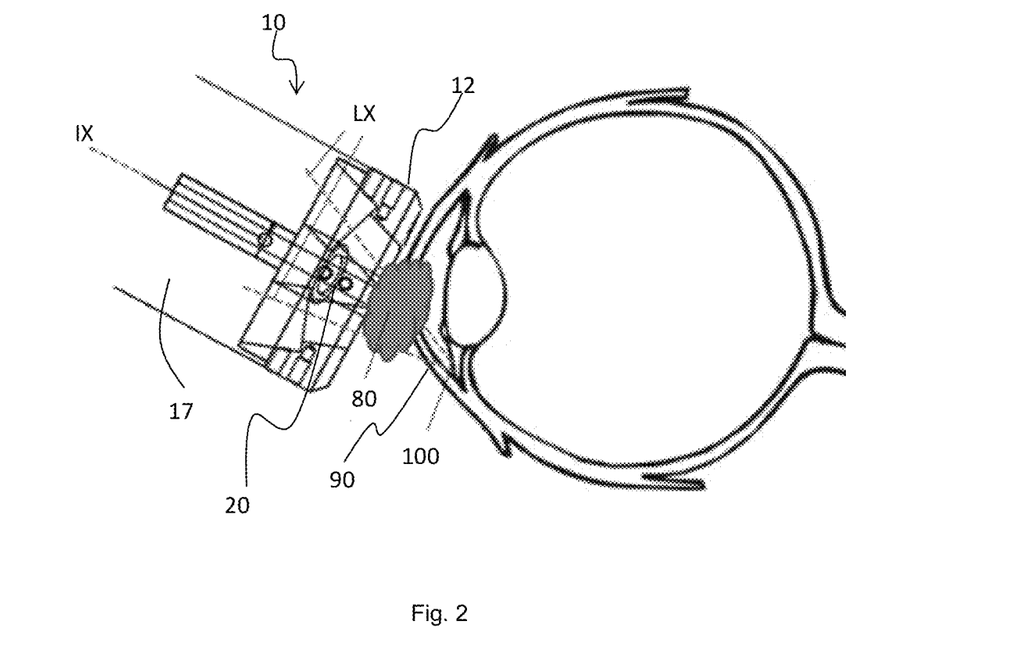
FIG. 2 is a longitudinal cross-sectional view of probe in use.

The probe 10 comprises a miniaturized charge-coupled device (CCD) camera 20 having an imaging lens at the distal end 12 of the probe 10, the camera 20 having an imaging axis IX as shown in FIG. 1. The distal end 12 of the probe 10 has a corneal contact surface 11 that is orthogonal to the imaging axis IX. The corneal contact surface 11 of the probe 10 is configured to be placed on the cornea 90 with an interfacing coupling gel 80 as shown in FIG. 2. The distal end 12 of the probe 10 is configured to support the optics and is built as a separate module. The probe 10 and camera 20 are connected via a flexible connection such as flexible wires to a processor which processes captured images for display on a display panel and/or storage in a media storage device.

Figure 3A:
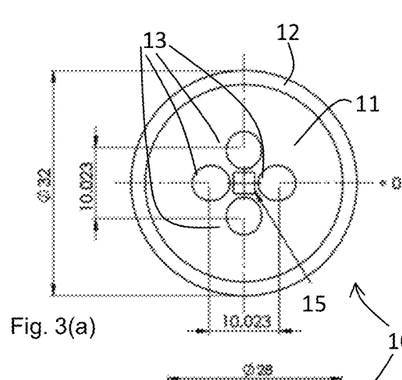
FIGS. 3(a) to (c) are orthographic views of a first embodiment of a distal end of the probe.
Figure 3B:
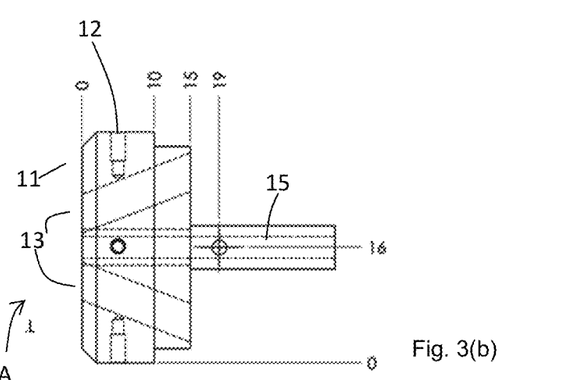
Figure 3C:
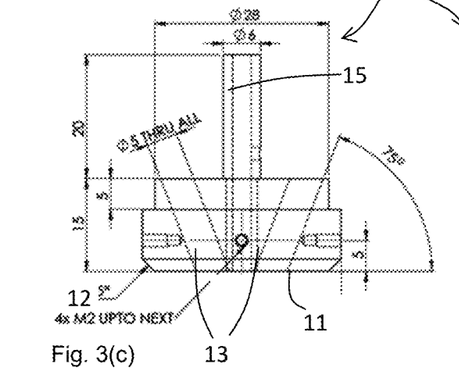
Figure 3D:
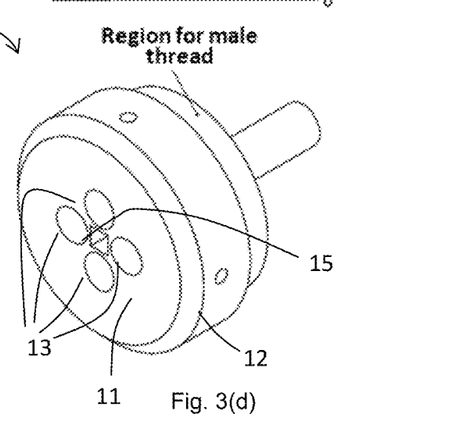
FIG. 3(d) is a perspective view of the first embodiment of the distal end.
Figure 3E:
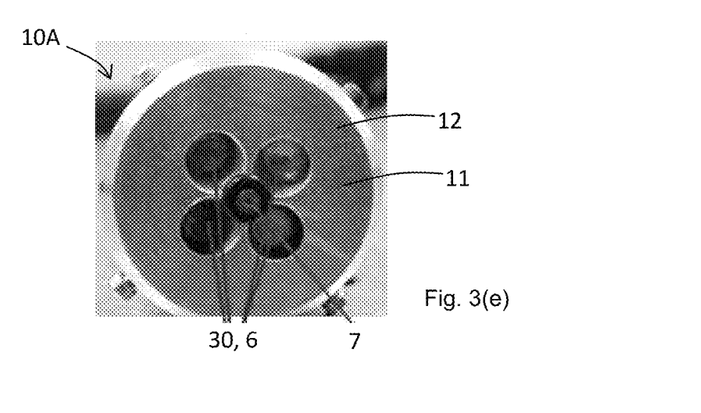
FIG. 3(e) is a photograph of the first embodiment of the distal end.
Figure 4A:
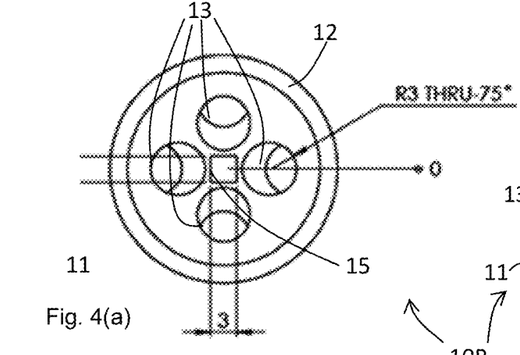
Figure 4B:
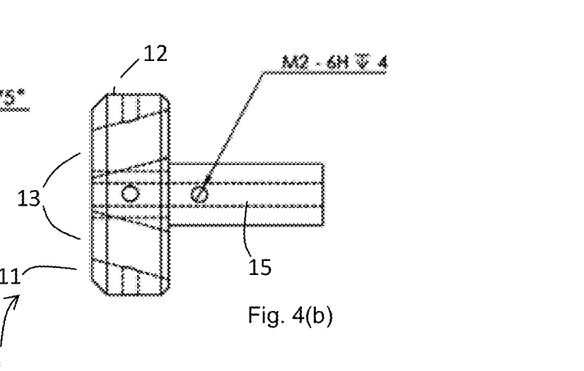
Figure 4D:
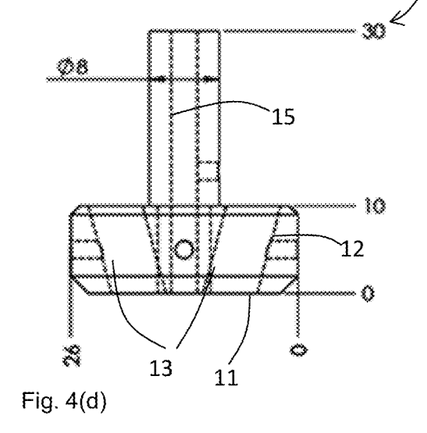
FIG. 4(d) is a perspective view of the second embodiment of the distal end.
Figure 4E:
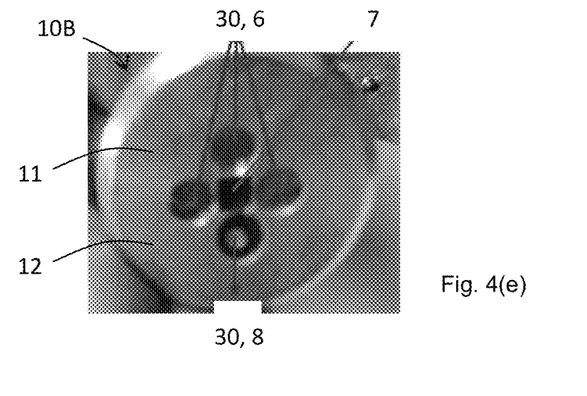
FIG. 4(e) is a photograph of the second embodiment of the distal end.
Figure 5A:
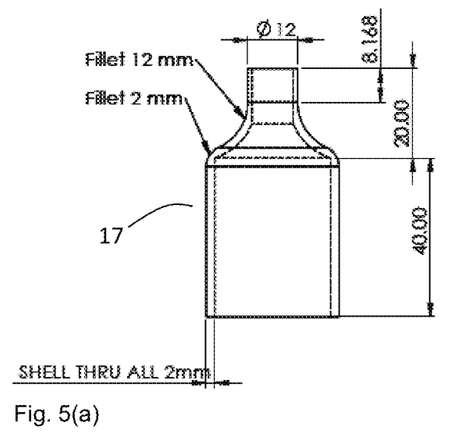
FIGS. 5(a) and (b) are orthographic views a sleeve of the probe.
Figure 5B:
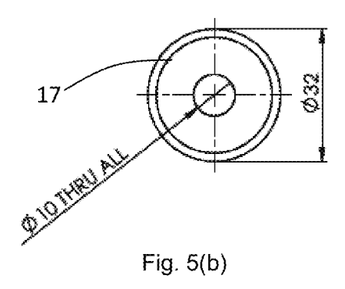
Figure 6:
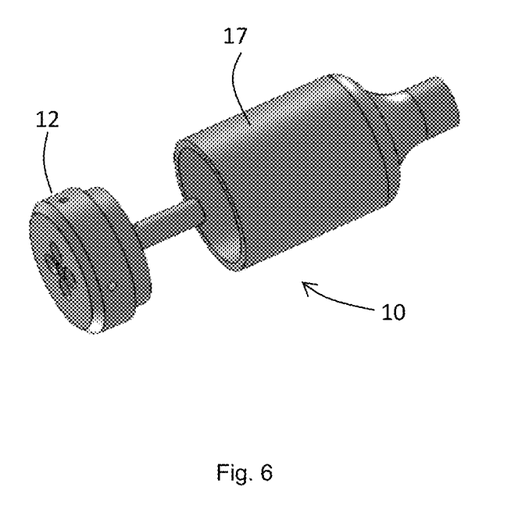
FIG. 6 is a perspective view of the sleeve.

Two probe embodiments 10A, 10B as shown in FIGS. 3 and 4 respectively were developed in which the distal end 12 of each probe 10 comprises the micro CCD camera 20 of diameter 3 mm and an array of illumination sources 30 which enable imaging of the iridocorneal region inside the eye. The distal end 12 of the first embodiment and second embodiment of the probe 10 has a diameter of 32 mm and 26 mm respectively. The probe 10 preferably includes a sleeve 17 as shown in FIG. 5 that facilitates easier handling of the probe 10 when assembled with the distal end 12 of the probe as shown in FIG. 6.

In every embodiment of the probe 10, there is preferably at least a pair of illumination sources 30 to enable complete illumination of the eye. The array of illumination sources 30 are arranged radially about the imaging axis and comprise at least one white light source and/or one Near Infra-Red (NIR) light source. The white light and NIR light source can be switched on alternately for illuminating the interior of the eye. Preferably, the illumination axis LX of each light source is offset at an angle from the imaging axis such that the imaging axis IX and illumination axis LX converge proximately in the interior chamber of the eye when the probe 10 is used. Further preferably, the pair of illumination sources 30 are configured to have controllable intensity.

In the first embodiment as shown in FIG. 3, the distal end 12 is formed with slots 13 configured to be provided with four white LEDs 6 as the illumination sources 30. In the second embodiment as shown in FIG. 4, the illumination sources 30 provided in slots 13 formed at the distal end 12 comprise three LEDs 6, of which two are white light sources and one is an NIR light source, and a fibre-optic NIR laser source 8 which is connected to the distal end 12 using an FC connector. The fibre-coupled NIR diode laser 8 emits a laser beam having a wavelength of 808 nm using a maximum power 2 mW. This power can be tuned using software. The tip of the FC-terminated fibre 8 can be seen in FIG. 4(e).

The LED viewing angle and orientation of the slots 13 provided at the distal end 12 to house the LED and/or NIR laser light sources 30 were optimised to obtain uniform illumination, based on a Lambertian approach, at the iridocorneal angle region. Positioning of the LEDs 6 and/or laser 8 is based on the Lambertian approach aimed to illuminate the targeted area in a controlled manner. By Lambertian, it is meant that uniform distribution of light emitted by the source (combination of LEDs 6) has the same brightness or luminescence when viewed from any angle. The distal end 12 of the first embodiment has four channels or slots 13 of internal diameter 5 mm for accommodating the LEDs 6 that are equally spaced around a central slot 15 for accommodating the CCD camera 20. The four slots 13 are drilled at an angle of 75° to the corneal contact surface 11 of the probe 10 surrounding the camera slot 15 so as to provide adequate illumination across the field of view of the micro CCD camera 20. The four slots 13 thus comprise illumination axes LX that are at an angle of 15° to the imaging axis IX as shown in FIG. 1.

An exemplary light source 30 such as the high luminous white light LED (LM520A, Seoul Semiconductor Co., Lt) used in the embodiments has a head diameter of 5 mm and viewing angle of 20° respectively. The viewing angle of the LED 6 is preferably between 10° to 30° for optimal performance. A potentiometer device is used to control illumination through each LED 6. The viewing angle and slot angle (75° to the corneal contact surface 11 of the probe 10) of the four LEDs 6 are designed such that the illumination region covers the targeted iridocorneal angle region 100 optimally and provides required luminescence throughout the region. Furthermore, the brightness of the LEDs 6 can be controlled by using a potentiometer.

The central channel or slot 15 of the distal end 12 comprising the imaging axis IX has an internal diameter 3 mm and is meant for a 3 mm×3 mm Micro CCD video camera 20 (for example the IntroSpicio™ 115, Medigus Ltd, Israel), which is employed as the image capturing device 20. The micro CCD camera 20 has an imaging lens optics at the distal end of the camera housing. The CCD camera 20 has a variable resolution with distance. Optical gel 80 is used as the interface medium between the camera 20 and the eye. The average corneal diameter is 11.77+/−0.37 mm in human males compared with 11.64+/−0.47 mm in human females. Hence the distance needed to be covered for imaging the angle region from the corneal surface is about 7-9 mm. At this distance, the image resolution of the camera 20 is about 60 μm which is sufficient for the specified application.

The main input to the device is 100-240 AC (auto switching). This video camera system is used together with a white light source 30 for eye imaging. The attainable spatial resolution of the probe system 10 naturally depends on the depth of field. The imaging probe 10 has variable resolution with respect to the distance between the object and camera head 7. For example, the resolution values at distances 5 mm, 10 mm and 15 mm from the camera head 7 are 50 mm, 62.5 mm and 90 mm respectively. By considering the distance of the camera head 7 from the angle region inside the eye and the refractive indices of the gel 80 and aqueous humor, the resolution value can be estimated to be around 60 micrometers for the anterior chamber angle imaging with the system or probe 10.

Figure 7:
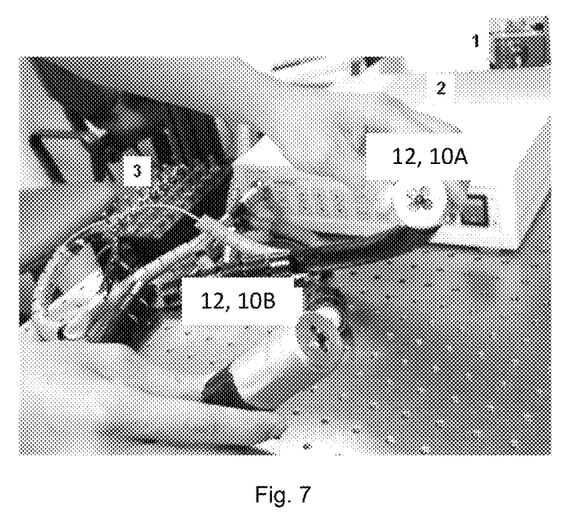
FIG. 7 is a photograph of two probes connected with connected with a fibre-coupled NIR laser, an LED driver and a camera driver.

FIG. 7 shows the two embodiments 10A, 10B of the probe 10 connected with a fibre-coupled NIR laser 1, an LED driver 2 and a camera driver 3. A video controller controls the video signal from and to a camera head 7 (visible in FIGS. 3(*e*) and 4(*e*)) of the camera 20. In use, the angle region 100 is initially identified using the white light source 30 provided by the LEDs 6. Subsequently, the NIR laser light source 8 is used to image the angle region 100. The slot angle and viewing angle of the LED and NIR light sources 30 are such that the focus area of the camera 20 has adequate illumination at the iridocorneal area for imaging capture. In order to image the angle region inside eye laterally, total internal reflection (TIR) of light rays at the corneal surface should be avoided. Notably, the camera 20 of the probe 10 is not in direct contact with the corneal surface 90 as a coupling gel 80 is used in between. With the use of a thin layer of a coupling gel 80 (e.g. Vidisic gel, Bausch & Lomb, NY, USA) which act as an optical interface between the eye and the micro CCD camera 20, TIR is avoided and hence the device or probe 10 can visualize structures in the anterior segment in a manner similar to direct gonioscopy. Users have the option to capture still images or record video stream from which images can be extracted and stored for later usage and analysis. The diameter of the distal end 12 of the probe 10 is suitable for compactness and easy handling, with sufficient working distance from the eye. The micro camera head 7 is connected to the video controller that controls the video signal from and to the camera head 7 by a cable.

Figure 8:
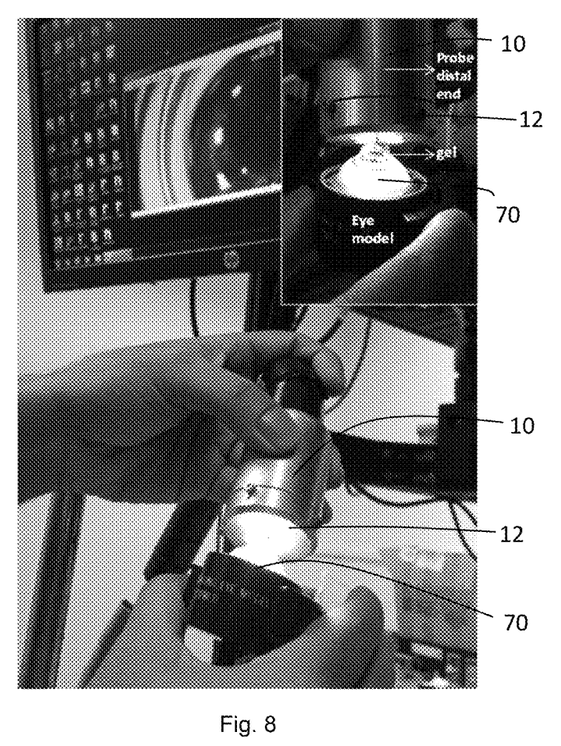
FIG. 8 is a photograph of a demonstration of imaging of an anterior chamber angle of an eye model using the probe with inset showing the distal end of the probe in contact with the eye model.
Figure 9A:
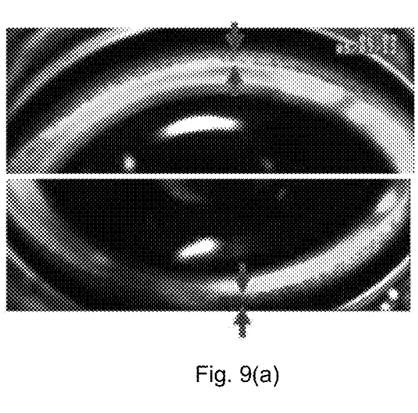
FIGS. 9(a) and (b) are images of an iridocorneal angle of an eye model obtained using the probe under light and dark conditions respectively.
Figure 9B:
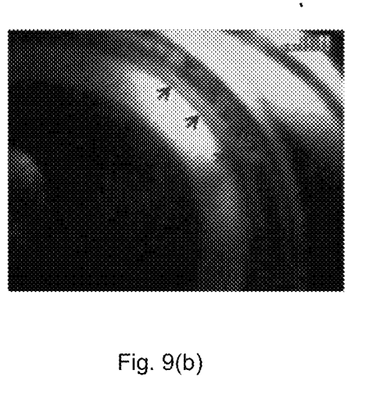
Figure 10A:
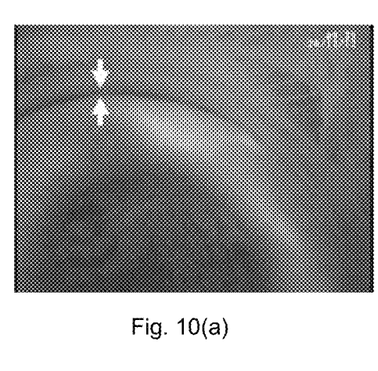
FIGS. 10(a) and (b) are images of an iridocorneal angle of a live rabbit eye obtained using the probe under light and dark conditions respectively.
Figure 10B:
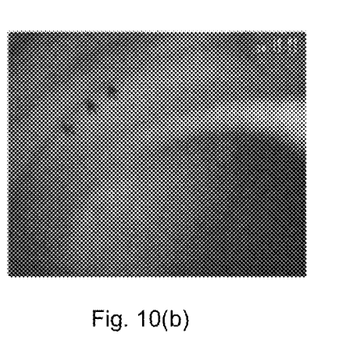

The probe 10 was refined using an eye or ocular model 70 (OEM-7, Ocular Instruments Inc., Bellevue, Wash.) as shown in FIG. 8 as well as pig eye samples, and subsequently tested on live rabbits. Fine quality images of the iridocorneal angle region 100 were obtained using the probe 10A with white LEDs 6. With a dual-modal probe 10B, imaging was performed on the ocular model using white visible LED 6 as shown in FIG. 9(*a*) and using NIR laser light source 8 alone as shown in FIG. 9(*b*), that is, under light and dark conditions respectively. Similarly, imaging was performed on live rabbit eye using white visible LED 6 as shown in FIG. 10(*a*) and using NIR laser light source 8 alone as shown in FIG. 10(*b*), that is, under light and dark conditions respectively. In both cases, the angle region 100 was noticeable, as indicated by the arrows in FIGS. 9(*a*) to 10(*b*). Imaging using the NIR light sources 8 avoid pupil constriction due to bright light (which occurs in the case of EyeCam™ imaging), thereby avoiding artificial altering in the anterior chamber angle[22] 100.

The developed hand-held imaging system or probe 10 can be used to continuously display, capture and record images of structures within a patient's eye, such as the iridocorneal angle 100. The whole system 10 can be transported easily. The system 10 can also be used for the treatment of glaucoma as landmark identification monitors during device implantation procedures. This instrument 10 can be a cheaper alternative to gonioscopic based angle detection as it can permanently document the angle findings through a photographic imaging technique with good quality images and will be an important adjunct requirement in clinical ophthalmology.

The proposed instrument 10 enables imaging of anterior chamber angle region 100 with wide-field coverage as well as in dual mode (in dark and light conditions). This device 10 can be connected to any desktop/laptop PC that is installed with the interfacing software. The PC interface is preferably USB. There is no need to carry the computer along with the system 10. Hence, this hand-held imaging system 10 can be commercialized without the display unit and can be transported easily. Thus, it is a cheaper alternative to gonioscopic or Retcam™ based angle imaging.

Advantages of the probe are given below:

1. No solid goniolens or prism is used in contact with the eye for imaging or measurement in contrast to gonioscopy which is a painful procedure as the goniscope has to be pressed against the eyeball to minimise TIR. With the present probe 10, a coupling gel 80 is used as an interfacing medium between the miniaturized camera 20 and eye.
2. The imaging probe 10 has variable resolution with respect to the distance between the object and camera head 7, thus allowing imaging of the anterior chamber angle region 100 as well as posterior segment of eye.
3. With a dual-modal probe 10B, imaging is performed in light (white visible LED ON) and dark (NIR laser light source alone) conditions and the angle region is noticeable in both cases.
4. Imaging using NIR light sources 8 avoid pupil constriction thereby avoiding artificial altering in anterior chamber angle 100.
5. Angle imaging using the probe 10 can be carried out when the patient is at sitting and supine postures.
6. CCD camera 20 is used to capture image or video to output for display and stored for later analysis. Most clinics do not document the angle through photography as it is cumbersome and requires time-consuming methods and expertise. These are not as flexible as the probe 10 of the present invention.
7. Only basic training is needed to handle the equipment. There is no need to train expert operators to use the probe 10.

Whilst there has been described in the foregoing description exemplary embodiments of the present invention, it will be understood by those skilled in the technology concerned that many variations in details of design, construction and/or operation may be made without departing from the present invention. For example, while the angle between the illumination axes and the corneal contact surface of the probe has been described above as being 75°, this angle may range from 70° to 78°.

REFERENCES

1. I. Agis, "The Advanced Glaucoma Intervention Study (AGIS): 7. The relationship between control of intraocular pressure and visual field deterioration," American Journal of Ophthalmology 130, 429-440 (2000).
2. W. M. Grant, and J. F. Burke Jr, "Why do some people go blind from glaucoma?," Ophthalmology 89, 991-998 (1982).
3. E. M. Stone, J. H. Fingert, W. L. Alward, T. D. Nguyen, J. R. Polansky, S. L. Sunden, D. Nishimura, A. F. Clark, A. Nystuen, and B. E. Nichols, "Identification of a gene that causes primary open angle glaucoma," Science 275, 668-670 (1997).
4. W. P. Nolan, J. L. See, P. T. Chew, D. S. Friedman, S. D. Smith, S. Radhakrishnan, C. Zheng, P. J. Foster, and T. Aung, "Detection of primary angle closure using anterior segment optical coherence tomography in Asian eyes," Ophthalmology 114, 33-39 (2007).
5. S. K. Seah, P. J. Foster, P. T. Chew, A. Jap, F. Oen, H. B. Fam, and A. S. Lim, "Incidence of acute primary angle-closure glaucoma in Singapore: an island-wide survey," Archives of ophthalmology 115, 1436-1440 (1997).
6. T. Aung, W. P. Nolan, D. Machin, S. K. Seah, J. Baasanhu, P. T. Khaw, G. J. Johnson, and P. J. Foster, "Anterior chamber depth and the risk of primary angle closure in 2 East Asian populations," Archives of ophthalmology 123, 527-532 (2005).
7. V. M. Murukeshan, V. K. Shinoj, S. P, and P. Padmanabhan, "Diagnostic Sensing of Specific Proteins in Breast Cancer Cells Using Hollow-Core Photonic Crystal Fiber," in *Multimodality Breast Imaging: Diagnosis and Treatment*, (SPIE PRESS), p. 572 (2013).
8. V. K. Shinoj, and V. M. Murukeshan, "Hollow-core photonic crystal fiber based multifunctional optical system for trapping, position sensing, and detection of fluorescent particles," Opt. Lett. 37, 1607-1609 (2012).
9. J. James, V. M. Murukeshan, and L. S. Woh, "Integrated photoacoustic, ultrasound and fluorescence platform for diagnostic medical imaging-proof of concept study with a tissue mimicking phantom," Biomedical Optics Express 5, 2135-2144 (2014), http://www.opticsinfobase.org/boe/abstract.cfm?URI=boe-5-7-2135.
10. J. G. Fujimoto, "Optical coherence tomography for ultrahigh resolution in vivo imaging," Nature biotechnology 21, 1361-1367 (2003).
11. T. Scheimpflug, "Improved method and apparatus for the systematic alteration or distortion of plane pictures and images by means of lenses and mirrors for photography and for other purposes," GB patent 1196, (1904).
12. R. Jain, and S. Grewal, "Pentacam: Principle and Clinical Applications," Journal of Current Glaucoma Practice 3, 20-32 (2009).
13. L. M. Sakata, R. Lavanya, D. S. Friedman, H. T. Aung, H. Gao, R. S. Kumar, P. J. Foster, and T. Aung, "Comparison of gonioscopy and anterior segment ocular coherence tomography in detecting angle closure in different quadrants of the anterior chamber angle," Ophthalmology 115, 769-774 (2008).
14. H. G. SCHEIE, "Width and pigmentation of the angle of the anterior chamber: a system of grading by gonioscopy," AMA archives of ophthalmology 58, 510-512 (1957).
15. N. G. Congdon, G. L. Spaeth, J. Augsburger, J. Klancnik Jr, K. Patel, and D. G. Hunter, "A proposed simple method for measurement in the anterior chamber angle: biometric gonioscopy," Ophthalmology 106, 2161-2167 (1999).
16. D. T. Quek, M. E. Nongpiur, S. A. Perera, and T. Aung, "Angle imaging: Advances and challenges," Indian journal of ophthalmology 59, S69 (2011).
17. A. L. Coleman, F. Yu, and S. J. Evans, "Use of gonioscopy in medicare beneficiaries before glaucoma surgery," Journal of glaucoma 15, 486-493 (2006).
18. R. Azad, T. Arora, R. Sihota, P. Chandra, D. Mahajan, S. Sain, and Y. Sharma, "Retcam fluorescein gonioangiography: a new modality for early detection of angle neovascularization in diabetic retinopathy," Retina 33, 1902-1907 (2013).
19. S. A. Perera, M. Baskaran, D. S. Friedman, T. A. Tun, H. M. Htoon, R. S. Kumar, and T. Aung, "Use of EyeCam for imaging the anterior chamber angle," Investigative ophthalmology & visual science 51, 2993-2997 (2010).
20. M. Baskaran, S. A. Perera, M. E. Nongpiur, T. A. Tun, J. Park, R. S. Kumar, D. S. Friedman, and T. Aung, "Angle assessment by EyeCam, goniophotography, and gonioscopy," Journal of glaucoma 21, 493-497 (2012).
21. V. K. Shinoj, V. M. Murukeshan, M. Baskaran, and T. Aung, "Note: A gel based imaging technique of the iridocorneal angle for evaluation of angle-closure glaucoma," Review of scientific instruments 85, 066105 (2014).
22. D. T. L. Quek, M. E. Nongpiur, S. A. Perera, and T. Aung, "Angle imaging: Advances and challenges," Indian journal of ophthalmology 59, S69 (2011).

The invention claimed is:

1. A hand-held probe for iridocorneal angle imaging of an eye, the hand-held probe comprising:
    a distal end having a flat corneal contact surface configured to be placed on a cornea of the eye;
    a single miniaturized charge-coupled device camera having a single imaging lens at the distal end of the hand-held probe and an imaging axis orthogonal to the flat corneal contact surface; and
    at least two illumination sources, each illumination source having an illumination axis at an angle to the flat corneal contact surface such that the imaging axis and the illumination axes converge in the eye to enable imaging of the iridocorneal angle,
    wherein the at least two illumination sources are configured to emit light with a uniform distribution based on a Lambertian approach, wherein the angle ranges from 70° to 78°, such that luminescence is the same when viewed from any angle.

2. The hand-held probe of claim 1, wherein the at least two illumination sources comprise four light sources provided radially about the imaging axis.

3. The hand-held probe of claim 2, wherein the four light sources comprise four LED.

4. The hand-held probe of claim 2, wherein the four light sources comprise at least one white light source and at least one NIR light source.

5. The hand-held probe of claim 4, wherein the at least one white light source and the at least one NIR light source are configured to allow the iridocorneal angle region of the eye to be illuminated by only one of the at least one white light source and the at least one NIR light source at any time.

6. The hand-held probe of claim 4, wherein the at least one NIR light source comprises at least one of: an NIR LED and a fibre-optic NIR laser source.

7. The hand-held probe of claim 1, wherein the camera is connected via a flexible connection to a processor configured to process captured images for at least one of: display on a display panel and storage in a media storage device.

8. The hand-held probe of claim 1, wherein the imaging axis and the illumination axes converge in the iridocorneal region of the eye.

9. The hand-held probe of claim 1, wherein the at least two illumination sources are configured to have controllable intensity.

10. A hand-held probe for iridocorneal angle imaging of an eye, the probe comprising:
a distal end having a flat corneal contact surface configured to be placed on a cornea of the eye;
a single miniaturized charge-coupled device camera having an imaging lens at the distal end of the hand-held probe and an imaging axis orthogonal to the flat corneal contact surface; and
at least two illumination sources, each illumination source having an illumination axis at an angle to the flat corneal contact surface such that the imaging axis and the illumination axes converge in the iridocorneal region of the eye, and wherein the hand-held probe is configured to image the iridocorneal angle of the eye.

11. The hand-held probe of claim 10, wherein the angle ranges from 70° to 78°.

12. The hand-held probe of claim 10, wherein the at least two illumination sources are configured to emit light with a uniform distribution such that luminescence is the same when viewed from any angle.

13. The hand-held probe of claim 10, wherein the at least two illumination sources comprise four light sources provided radially about the imaging axis.

14. The hand-held probe of claim 13, wherein the four light sources comprise four LED.

15. The hand-held probe of claim 13, wherein the four light sources comprise at least one white light source and at least one NIR light source.

16. The hand-held probe of claim 15, wherein the at least one white light source and the at least one NIR light source are configured to allow the iridocorneal angle region of the eye to be illuminated by only one of the at least one white light source and the at least one NIR light source at any time.

17. The hand-held probe of claim 15, wherein the at least one NIR light source comprises at least one of: an NIR LED and a fibre-optic NIR laser source.

18. The hand-held probe of claim 10, wherein the camera is connected via a flexible connection to a processor configured to process captured images for at least one of: display on a display panel and storage in a media storage device.

* * * * *